United States Patent [19]

Adolfsen et al.

[11] Patent Number: 4,839,276
[45] Date of Patent: Jun. 13, 1989

[54] INTERFERENCE - RESISTANT LIPOSOME SPECIFIC BINDING ASSAY

[75] Inventors: Robert H. Adolfsen, Montrose; Eddie Hedaya, Hartsdale; C. Lam Mak, Valley Cottage; Moshe Schwarzberg, Hastings-on-Hudson, all of N.Y.

[73] Assignee: Technicon Instruments Corporation, Tarrytown, N.Y.

[21] Appl. No.: 678,531

[22] Filed: Dec. 5, 1984

[51] Int. Cl.$^4$ .................. G01N 33/53; G01N 33/543; G01N 33/554
[52] U.S. Cl. .......................................... 435/7; 435/18; 436/518; 436/519; 436/821; 436/825; 436/829
[58] Field of Search ............... 436/508, 509, 821, 825, 436/829; 435/7, 18; 536/22, 117; 424/312–361

[56] References Cited

U.S. PATENT DOCUMENTS

| | | | |
|---|---|---|---|
| 4,193,983 | 3/1980 | Ullman et al. | 436/829 X |
| 4,342,826 | 8/1982 | Cole | 436/829 X |
| 4,403,042 | 9/1983 | Henry et al. | 436/825 X |
| 4,446,231 | 5/1984 | Self | 435/7 |
| 4,609,630 | 9/1986 | Yanovsky | 436/825 X |
| 4,698,299 | 10/1987 | Janoff et al. | 436/825 X |

OTHER PUBLICATIONS

Alving, C., Biochem. Soc. Trans. 12:342–344 (1984).
Mold, C. et al., Journ. of Immunol., 125:696–700 (1980).
Strejan, G. H. et al., Journ. of Immunol., 123:370–378 (1979).
Lafer, E. M. et al., Journ. Exp. Med., 153:897–909 (1981).

Primary Examiner—Robert I. Warden
Assistant Examiner—Jack Spiegel
Attorney, Agent, or Firm—Jeffrey M. Greenman

[57] ABSTRACT

A method and reagent composition provide for the removal or blocking of serum interferences in liposome immunoassays. A carrier or liposome exhibiting at least one domain of phosphoryl ester groupings different from those of the marker liposome is introduced into the reaction mixture, whereby endogenous interfering species competitively bind to such carrier or liposome rather than to the marker liposome. Also, soluble phosphoryl ester groupings can be introduced into the reaction mixture which react with such endogenous species and further reduce serum interferences.

20 Claims, No Drawings

INTERFERENCE - RESISTANT LIPOSOME SPECIFIC BINDING ASSAY

BACKGROUND OF THE INVENTION

1. Field of the Invention

This invention relates to the field of specific binding assays, particularly immunoassays for determining substances of clinical interest. Specific binding assays are based on the specific interaction between a ligand, i.e., a bindable analyte under determination, and a binding partner therefor, i.e., receptor. Where one of the ligand and its binding partner is a hapten or antigen and the other is a corresponding antibody, the assay is known as an immunoassay.

2. Brief Description of the Prior Art

Many properties of natural cell membranes can be duplicated in simple lipid bilayer systems, referred to as liposomes. One of these properties is lysis. When a vesicular, e.g., liposome, membrane contains an externally accessible antigen, it will react with its corresponding antibody. When the antigen-sensitized liposome reacts with corresponding antibody in the presence of complement, the membrane is irreversibly damaged and can no longer function as an intact selective permeability barrier. This is immunolysis.

The extent of immunolysis has been monitored by using antigen-sensitized liposomes containing any of a wide variety of entrapped marker molecules which are released upon immunolysis. See Hixby, et al., Proc. Nat. Acad. Sci., 64: 290-295 (1969); Kinsky, et al., Biochemistry, 8: 4149-4158 (1969); Kinsky, et al., Biochemistry, 9: 1048 (1970). See also Six, et al., Biochemistry, 13: 4050 (1974); Uemura, et al., J. Biochem, 87: 1221 (1980); and Uemura, et al., J. Immunol. Methods, 53: 221-232 (1982); Kataoka, et al., Biochem. Biophys. Acta, 298: 158-179 (1973); Haga, Biochem, Biophys. Res. Comm., 95: 187-192 (1980); Solomon, et al., Biochem., Biophys. Acta, 455: 332-342 (1976); Tokunaga, et al., FEBS Letters, 106: 85-88 (1979) and Magee, et al., J. Cell Biology, 63: 492-504 (1974).

Specific binding assay systems have been proposed, using a liposome which has been prepared or treated to have surface-bound ligand or ligand analog and a marker or reagent substance enclosed within the vehicle. The remaining reagents for the assay include (1) a binding partner, e.g., antibody, for the ligand and (2) complement to effect lysis of the vesicle upon binding of the binding partner to surface-bound ligand. Generally, see Gregoriadis, et al., *Liposomes in Biological Systems,* John Wiley & Sons, N.Y. (1980), especially Chapter 12 entitled "Liposomes as Diagnostic Tools".

Also, immunoassay systems have been disclosed in which the use of an enzyme-encapsulating liposome is suggested. Hsia, et al., U.S. Pat. No. 4,235,792 describes a competitive homogeneous immunoassay method which employs immunolysis of an antigen-sensitized liposome containing a marker. Enzymes are among the markers disclosed (col. 6, lines 24-28). Cole U.S. Pat. No. 4,342,826 discloses a specific binding assay using an antigen-sensitized, enzyme-containing liposome. These liposomes are immunospecifically caused to expose enzyme upon binding of corresponding antibody and fixing of active complement. Upon enzyme exposure, the presence or absence of enzymatic activity is detected. Cole emphasizes the advantage of providing a homogeneous system in which enzymic activity is substantially greater upon lysis, e.g., a "signal:noise" ratio of at least 5-10 and preferably above 60.

Interferences in immunoassays can result from a variety of interactions between the sample and the marker. For example, where the marker is an enzyme, interference can result due to the presence of endogeneous enzymes, non-specific binding proteins and enzyme inhibitors in the sample. These interferences can be eliminated by judicious selection of a suitable marker, the addition of blocking agents and/or sample pretreatment steps. Cole describes the separate and independent pretreatment of the sample prior to performance of an assay. However, it is not the purpose of this invention to address these known interferences or techniques for avoiding the same.

Rather, in liposome immunoassays, we have observed a new class of interferences which appear to be due to interactions between the sample and the membrane of the liposome which encapsulates the marker. Certain constituents of the sample appear to bind with the membrane of the liposome and lead to false results which can be higher or lower than is attributable to the antibody-dependent immuno lysis. Whether such false result is higher or lower depends upon the manner in which the interfering substance affects the liposome membrane. The prior art does not provide or suggest means to eliminate these types of interferences.

SUMMARY OF THE INVENTION

In contrast to the prior art, the present invention provides a novel method and reagent composition for performing liposome immunoassays wherein the effects of sample interferences are minimized and which does not require sample pretreatment to achieve such result. Thus, the present composition is particularly suitable for automated analytical systems and for analyte determinations requiring large sample volumes, i.e., those in which the effects of such interferants are not diluted out.

The specific binding assay method of the invention comprises the steps of mixing with said sample a first, or marker, liposome containing a marker and having a surface bound ligand or cross-reactive ligand analogue of the analyte to be assayed and the respective binding partner to form a reaction mixture, in the presence of complement, for assaying said analyte, and further concurrently mixing a carrier or second liposome into the reaction mixture which expresses at least one domain of phosphoryl ester groupings different from the phosphoryl ester groupings of said first liposome. Any endogenous species in said reaction mixture, which would tend to bind or interfere directly with the first liposome, competitively bind to the second liposome rather than to the first liposome so as to enhance the accuracy of immunoassay.

The present invention further provides a reagent composition for determining a ligand in a liquid sample, which comprises: (a) a binding partner for said ligand, (b) a selectively accessible first liposome having a ligand or cross-reactive ligand analogue incorporated within its membrane and expressing predetermined domains of phosphoryl ester groupings; (c) a substance (complement) which modifies vesicle accessibility in response to binding of the membrane-incorporated ligand or ligand analogue with its binding partner; (d) a marker contained in the first liposome to indicate modified permeability of the first liposome; (e) a carrier or second liposome which expresses at least one domain of phosphoryl ester groupings different from the domains expressed by said first liposome.

The invention is exemplified by comparison of the accuracies of specific binding assays in which said reaction mixture either incorporates or does not incorporate the second liposome composition. Such comparison indicates that incorporation of the second liposome provides an assay of much improved accuracy, based on correlation with a reference radioimmunoassay.

Still further improvements in accuracy are achieved by also including the step of introducing soluble esters of a phosphoric acid into said reaction mixture to provide phosphoryl ester groupings in solution.

DESCRIPTION OF THE PREFERRED EMBODIMENTS

Specific terms in the following description which refer only to a particular embodiment are exemplary of all of the embodiments, unless otherwise indicated.

Sample fluids on which immunoassays may be performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Other sources of sample fluid which are tested by conventional methods are contemplated as within the meaning of this term as used and can, likewise, be assayed in accordance with the invention.

The term "ligand" refers to any substance, or class of related substances, whose presence can be qualitatively or quantitatively determined in a sample fluid by an immunoassay, such as those just described. The term "cross-reactive ligand analog" refers to a substance which is not identical to a ligand but has the same binding, e.g., immunological specificity. For example, in an assay for gentamicin, it is known that, with appropriate antiserum, the reagent composition can employ gentamicin itself or sisomycin which cross-reacts. The present method can be applied to the assay of ligands for which there is a specific binding partner and, conversely, to the determination of the capacity of a liquid medium to bind a ligand (usually due to the presence of a binding partner for the ligand in the sample). The ligand usually is a peptide, protein, carbohydrate, glycoprotein, steroid, or other organic molecule for which a specific binding partner exists or can be provided by immunological or synthetic means. The ligand, in functional terms, is usually selected from antigens and antibodies thereto, haptens and antibodies thereto, and hormones, vitamins, metabolites and pharmacological agents, along with their receptors and binding substances and normal serum constituents and disease markers.

The terms "binding partner" or "receptor" refers to any substance, or class of substances, which has a specific binding affinity for the ligand in preference to other substances. In the majority of assays herein discussed, the reagent incorporates components which interact with the ligand or its binding effectors in the sample in an immunochemical manner. That is, there is an antigen-antibody or hapten-antibody relationship between reagent and the ligand or its binding effector in the sample. However, it is well understood in the art that other binding interactions between the ligand and its binding partner serve as the basis of specific binding assays, including the binding interactions between hormones, vitamins, metabolites, an pharmacological agents, and their respective receptors and binding substances. For example, polypeptide hormone receptors as binding agents or partners are discussed in Langan, et al., (Eds.), *Ligand Assay*, Masson Publishing U.S.A. Inc., New York, pages 211 et seq (1981).

The term "selectively accessible vesicle" refers to single or multi-compartmented sacs enclosing an internal volume, having a wall composed of one or more components and forming one or more internal closed compartments. One example of such a vesicle is a cell ghost, formed by opening a cellular membrane, removing the internal components of the cell and resealing the membrane. Another example is a liposome, which can be a single- or multi-compartmented vesicle comprised of lipids, particularly lipid mixtures including at least one phospholipid, which form a continuous single or bilayer sealed lipid membrane. Additional common constituents of these lipid mixtures are cholesterol and charged long chain phosphates. Liposomes can be prepared by any of a number of techniques. For example, multilamellar vesicles can be prepared by film evaporation and hydration of a lipid film and also by reverse phase evaporation techniques. For a general overview of liposomes and their preparation, reference is made to Papahadjopoules, et al., (Eds), Liposomes, Ann. N.Y. Acad. Sci., volume 308 (1978); Tom, et al., (Eds.), *Liposomes and Immunobiology*, Elsevier North Holland Inc., N.Y. (1980); and Gregoriadis, et al., *Liposomes in Biological Systems*, John Wily & Sons, N.Y. (1980).

Liposomes used in immunoassays are prepared to have surface-incorporated ligand or ligand analog moieties. Such liposomes are formed using ligand-amphiphile conjugates, which usually takes the form of a ligand-coupler-amphiphile molecule. Amphiphiles are substances which contain both water soluble and water insoluble regions. Such substances are best exemplified by lipid amphiphiles, such as the phosphatidyl ethanolamines, phosphatidyl serine, phosphatidyl inositol, sphingomyelin cerebrosides, phosphatidic acid, plasmalogens, cardiolipins and fatty acids. When liposomoes are preformed, chemical functionalities can exist at their external surface to which receptors of the ligand to be assayed may be covalently linked. Appropriate reactions which may be applied to effect such linkage are described in Williams et al., *Methods in Immunology and Innumochemistry*, Vol. 1, Academic Press, New York (1967). In some cases, antigens may be adsorbed to the liposome surface, as was shown by Uemura and Kinsky, Biochemistry, 11: 4085–4094 (1972).

To perform a liposome immunoassay of the invention, complement is normally present, which modifies vesicle accessibility in response to binding of surface-incorporated ligand or ligand analog and the binding partner. Normally, because of this charge, the phosphoryl head-groups in the liposome membrane are oriented outwards towards the aqueous medium. For example, in the phosphatidyl choline head-group, there is negative charge on the phosphate moiety and a positive charge on the choline moiety. In addition, the surface bound ligand or ligand analog is oriented outwards towards the aqueous medium and can become bound by antibody. Binding of two such antibodies of the $I_gG$ class in close proximity on the external surface of the membrane leads to fixation of complement and subsequent lysis. An additional requirement is that the two $I_gG$ antibodies belong to one or more of the subclasses which are capable of fixing complement. However, only one antibody of the $I_gM$ class is required to fix complement and induce lysis. For a general ovrview of complement and its effects, see Rapp, et al., *Molecular Basis of Complement Action,* Appleton-Century-Crofts, New York (1970). Also, the role of complement is discussed in many of the references addressing other liposome immunoassays which have been cited above.

The method can employ any of the variety of detection systems for monitoring immunolysis, including those described in the references cited above. The latter detection system includes a stable nitroxide or fluorescent marker, whose signal intensity increases as a consequence of immunolysis. Additionally, as initially shown by Kinsky et al., supra., enzyme substrates can be entrapped within the liposome, which react with an enzyme to generate a measurable condition when lysis allows intermixing with the corresponding enzyme. The reverse configuration, i.e., where enzyme is entrapped within the liposome and substrate is introduced into the reaction mixture, can also be employed. Owing to their high sensitivity and the variety of enzyme/substrate combinations available, the use of enzymes is desirable. Such enzymes include, for example, alkaline phosphatase, galactosidase, glucose oxidase, dehydrogenases, urease, and various proteases. In co-pending U.S. patent application Ser. No. 528,496, which was filed on Sept. 1, 1983 and is assigned to a common assignee, a novel variant is employed, where entrapped peroxidase is more active towards the substrate system when the liposome is intact than when it is lysed. This phenomenon is believed to involve the conversion of a permeable substrate (hydrogen peroxide) to a reactive intermediate which passes through the membrane and oxidizes a second component of the substrate system to provide a chemiluminescent signal. Lysis leads to inhibition of the entrapped enzyme and reduced signal. Also, multiple enzyme systems can be employed where the entrapped enzyme produces a product on lysis which serves as a substrate for a second enzyme present in the reaction mixture. For examle, the entrapped enzyme may be glucose oxidase which generates hydrogen peroxide, which serves as substrate for peroxidase. Multiple enzyme systems have advantages with respect to sensitivity and reduced background signal.

Reference is hereafter made to the term "empty" liposome. Such term refers to a liposome which, in contrast to those described above, does not contain any component of the detection system therein or ligand on the surface thereof. The volume enclosed by the membrane of the empty liposome may contain salts, buffers and other materials, such as carbohydrates, phosphate ester compounds and proteins.

Interferences with liposome immunoassays are generally of the types which induce nonspecific lysis of the liposome and those which inhibit the immunolysis by the specific antibody and active complement. Such interferences are caused, in part, by the binding of sample constituents to the liposome membrane and are addressed by this invention.

One class of binding constituent which may exist in human serum are natural antibodies against phospholipids and liposomes, for example, as discussed in C. Alving, Biochem. Soc. Trans., page 342 (1984). Such natural antibodies have been shown to be present in about ten percent of apparently normal human serum samples and have not been associated with any particular disease state. Further, such natural antibodies can fix complement as a consequence of binding to liposomes, which leads to nonspecific lysis. A sample containing such natural antibodies will, therefore, generate a signal associated with an enhanced lysis and tend to lower the estimate of ligand concentration in the sample.

Antibodies against nuclear material, such as DNA, are associated with certain autoimmune diseases. Such antibodies can display specificity for domains of phosphate ester groups which bridge the nucleosides of DNA. Hence, they may also cross-react or bind to areas of the liposome surface with exposed phosphate ester groups. Such binding can lead to either activation of complement and resulting immunolysis or, conversely, inhibit complement activation by blocking ligand-binding sites on the exposed membrane surface of the liposome.

Still another class of binding constituents which may exist in human serum are peptides, lipoproteins and proteins other than natural antibodies. One example is the globular protein, C-reactive protein (CRP), which is generated endogenously in inflammatory states and is capable of fixing complement upon the binding to the membrane of liposomes. Consequently, lysis results and tends to lower the estimate of the assay ligand concentrations in the sample.

Also, the binding to the liposome membrane of natural antibodies or other sample constituents which are incapable of activating complement can lead to the inhibition of specific immunolysis. When such binding occurs in the vicinity of a ligand group on the membrane surface, it can result in the hinderance of the binding of the ligand by the corresponding antibody or in the reduction in the probability of occurrence of antibody/ligand pairs required for complement activation. In this case, the inhibition of specific immunolysis will provide an estimate of ligand concentration in the sample which is falsely high.

In general, interferences of the types described above become more severe as the concentration of serum in the assay increases and, thus, will be found more often in assays of lower-concentration analytes which require higher sensitivity such as for therapeutic drugs, e.g., digoxin,, where erroneous reports can lead to potentially fatal consequences.

Cardiolipin antigen is a phospholipid which is known to be specific for syphillis tests. Antibodies to cardiolipin have been shown to cross-react with DNA and phospholipids. Reference is made to Cuarnier, *Biochem. Biophys. Acta.,* Vol. 58, page 347 (1974) and to *Lipids,* Vol. 9, page 692 (1974). These references suggest that antibodies to phospholipids and other compounds featuring phosphate ester groups have limited specificities. We have observed that natural antibodies or non-antibody serum constituents also exhibit limited specificity to phospholipids and other compounds featuring phosphate ester groups and, therefore, their binding to "marker" liposome could be blocked by certain phospholipid and phosphate ester compositions introduced into the reaction mixture and not forming part of the detection system.

For example, such interferences are, at least, partially eliminated by the use of an "empty" liposome featuring lipid composition analogous with that of the ligand-bearing or "marker" liposome. However, when the "empty" liposome was made to incorporate cardiolipin or a non-cross-reactive ligand analog, such interferences were substantially reduced. It is believed that such "empty" liposome presents a domain, including not only the specific phospholipid to eliminate the interferences, but also exhibit a perturbed membrane structure which enhances the binding of such interferences. That is, the binding of the interfering substance in serum is enhanced by incorporating the cross-reacting additive within a bilayer membrane or the "empty" liposome which provides a domain of higher reactivity to the interfering serum constituent.

Furthermore, a combination of cardiolipin liposome and a soluble phosphate ester, such as phosphoryl choline or uridine-2',3'-cyclic phosphate ester, can be employed to significantly eliminate all such interferences in the immunoassay. Of particular importance is the fact that neither cardiolipin nor the uridine phosphate has any structural similarity with the head groups on the ligand-bearing liposome, except for the presence of a phosphate ester group.

It is conceivable that other empty liposomes can be made to eliminate such interferences in an immunoassay, for example, by manipulation of the lipid composition of the membrane and/or the addition of membrane-soluble components and head groups of the membrane. Carriers other than empty liposomes could be used for the expression of these groups. For example, phospholipids and phosphate esters could be immobilized onto soluble polymers or particulate materials other than liposomes and introduced into the reaction mixture for such purposes.

EXAMPLE I

This Example illustrates the correlation with radioimmunoassay of a $T_4$-liposome immunoassay, in the absence of interferant-removing additives, such as an "empty" liposome and phosphoryl choline.

REAGENTS $T_4$-sensitized liposome containing beta-galactosidase enzyme was prepared in a flask by mixing 220 ul of egg lecithin (Sigma Chemical Co., Palo Alto, CA), 5.25 mg dicetyl phosphate, 8.70 mg cholesterol, 0.65 mg DL-alpha-tocopherol and 2.19 mg $T_4$ conjugate in 100 ml chloroform. The $T_4$ conjugate was prepared as described in Hsia, supra. A lipid film was formed on the inner surface of the beaker by evaporating the mixture at 40° C. on a rotary evaporator and was further dried under a high vacuum system at room temperature for one hour. Liposomes were formed by the hydration of the lipid film with 6 ml cold enzyme solution (18.1 mg $\beta$-galactosidase, 13 ml of 50 mM TRIS buffer, pH 7.5) with rotation. The $T_4$ liposome containing $\beta$-galactosidase enzyme was separated from extravesicular enzyme by centrifugation. The purified liposome preparation (6 ml) was diluted to 1:150 in TRIS buffer (50 mM, pH 7.5) and stored at 4° C. in the dark.

Complement reagent was prepared by reconstituting one vial of lyophilized guinea pig serum (Pel Freeze, Rogers, AK) with 3 ml distilled water.

Rabbit anti-thyroxine antiserum was heated at 57° C. for 30 minutes and the harvested antiserum diluted to 1:60 with 50 mM barbital buffer (pH 8.5) to provide a stock solution.

The assay buffer solution was 50 mM barbital buffer (pH 8.5) containing 120 mM NaCl, 1 mM $MgCl_2$, 0.15 mM $CaCl_2$, 0.5% BSA and 0.05% $NaN_3$.

Thyroxine human serum standards (1.5, 3, 6, 12, 24 ug/dl) was prepared from a stock thyroxine solution of 10 mg thyroxine free acid (Sigma, supra) dissolved in 50 ml 0.2N NaOH. Appropriate dilutions were made using commercially available human serum.

Substrate and $T_4$-releasing agent (to free bound $T_4$) solution was prepared by mixing 18.5 mg O-nitrophenyl-B-galactoside ("ANS", Sigma, supra), hereafter referred to as "ANS" stock solution, and 3.0 mg of 8-anilino-naphthalene-1-sulfonic acid ammonium salt (Eastman Organic Chemicals, Inc., Rochester, NY) in 10 ml barbital buffer.

Reagent A was prepared by combining 235 ul of "substrate" and "ANS" stock solution with 30 ul (1:60) antibody and 85 ul barbital buffer. The preparation was scaled up to provide sufficient reagent for multiple testing.

Reagent B was prepared by combining 50 ul (1:150) liposome preparation with 40 ul of complement. Here again, the preparation was scaled up to provide sufficient reagent for multiple testing.

ASSAY PROCEDURE AND RESULTS

A 200 ul volume each of the $T_4$ standards and 20 clinical samples were pipetted individually into cuvettes on the cuvette tray of a Technicon RA-1000 analytical system (Technicon Instruments Corporation, Tarrytown, NY). Reagent A and reagent B were placed in the reagent tray of such system. The system was programmed to automatically pipette and incubate 20 ul of each sample and also standard each with 350 ul of reagent A for three minutes at 37° C. before the addition of 90 ul of reagent B. The solutions were further incubated for five minutes at 37° C. before the rates of increase of optical density were monitored, using a 405 nm optical filter. The $T_4$ values of the clinical samples were then calculated based on the rate of change in optical density which occurred at different levels of $T_4$. A comparison of the $T_4$ values of the clinical samples determined by liposome immunoassay (LIA) and radioimmunoassay (RIA) showed that numerous data points were obtained which did not correlate with the value obtained by analysis of the same sample with the RIA techniques. Further, such values in their entirety did not correlate with those obtained with RIA techniques. (A correlation coefficient of only 0.638 was obtained.) Also, such lack of correlation indicates the effects of interfering substances in the non-correlating samples.

EXAMPLE II

Numerous serum samples, which were not correlated with RIA, showed anti-liposomal activity when combined with $T_4$-liposomes and complement.

This example illustrates the effects of "empty" liposome, cardiolipin "empty" liposome and triiodothyronine ($T_3$)-bearing "empty" liposome on the high lytic activity associated with such samples (outlier samples).

REAGENTS $T_4$-$\beta$-galactosidase liposomes used in this experiment were prepared as described in Example I.

"Empty" liposomes were prepared as described in Example I for the $T_4$-$\beta$-galactosidase liposome, except that the lipid mixture and hydration solution contained no $T_4$-conjugate or B-galactosidase enzyme, respectively. The empty liposome preparation was diluted 1:30 before use.

Cardiolipin "empty" liposomes were prepared as described in Example I for $T_4$-$\beta$-galactosidase liposome, except that the lipid mixture contained 3.95 mg of cardiolipin instead of 2.19 mg of $T_4$-conjugate and the hydration solution contained no B-galactosidase enzyme. The cardiolipin "empty" liposome preparation was diluted 1:30 before use.

"Empty" T$_3$-liposomes were prepared as described in Example I for T$_4$-β-galactosidase liposome, except that the lipid mixture contained 4.1 mg of T$_3$ conjugate instead of 2.19 mg of T$_4$ conjugate and the hydration solution contained no β-galactosidase enzyme. The "empty" T$_3$-liposome preparation was diluted 1:30 before use.

Complement reagent was from the same source as described in Example I. The complement solution was prepared by mixing one vial of lyophilized material with 3 ml of distilled water.

Substrate and T$_4$ releasing agent in buffer were prepared, as described in Example I.

Reagent A was prepared by combining 235 ul of "substrate" and "ANS" stock solution with 115 ul of barbital buffer. Note: Reagent A does not contain anti-T$_4$ antibody as did Reagent A in Example I.

Reagent B was prepared as described in Example I.

ASSAY PROCEDURE AND RESULTS

First, 25 ul volumes of buffer were pipetted into individual cuvettes of the cuvette tray of a Technicon RA-1000 analytical system, supra. Then, an equal number of 25 ul volumes of different serum samples were pipetted into other cuvettes of the same tray. A 200 ul volume of preparations of "empty" liposome (1:30), cardiolipin "empty" liposome (1:30), "emtpy" T$_3$-liposome (1:30) or buffer were dispensed into each different sample cup of the sample tray and Reagents A and B were placed in the reagent tray of such system. The system was programmed to automatically pipette 30 ul of each preparation with 350 ul of Reagent A to the appropriate cuvette and incubate for three minutes at 37° C. before the addition of 90 ul of Reagent B. The solution was further incubated for five minutes at 37° C. before the rates of increase in optical density were monitored using a 405 nm optical filter. The serum blank (without antibody) of each outlier sample in the presence of "empty" liposome, cardiolipin "empty" liposome, "empty" T$_3$-liposome and buffer were recorded. The results were as set forth in Table I below.

The procedure described above was repeated with -galactosidase-T$_4$-liposome and cardiolipin "empty" liposomes, which were similarly prepared except that the cardiolipin "empty" liposome and uridine phosphate (uridine 2',3'-cyclic phosphate ester) were included in the formulation of Reagent A. The results of this experiment were as set forth in Table II.

TABLE I

| | Rate (Absorbance/Minute) β-Galactosidase-T$_4$—Liposome | | | |
|---|---|---|---|---|
| Serum Sample | In Buffer | "Empty" Liposome | Cardiolipin "Empty" Liposome | Empty T$_3$—Liposome |
| 1 | 0.0678 | 0.0652 | 0.0354 | 0.0242 |
| 2 | 0.0463 | 0.0326 | 0.0272 | 0.0223 |
| 3 | 0.0623 | 0.0463 | 0.0231 | 0.0248 |
| 4 | 0.0675 | 0.0460 | 0.0246 | 0.0228 |
| None | 0.0220 | | | |

TABLE II

| | Rate (Absorbance/Minute) β-Galactosidase-T$_4$—Liposome | | | |
|---|---|---|---|---|
| Serum Sample | In Buffer | Uridine Phosphate (8 mM) | Cardiolipin "Empty" Liposome | Uridine Phosphate and Cardiolipin "Empty" Liposome |
| 1 | 0.1199 | 0.0693 | 0.0646 | 0.0519 |
| 2 | 0.1193 | 0.0807 | 0.0530 | 0.0466 |
| 3 | 0.0868 | 0.0593 | 0.0463 | 0.0448 |
| None | 0.0419 | | | |

Under the conditions of this Example, which were run in the absence of the T$_4$ antibody significant rates of increasing optical density associated with the outlier samples were reduced in the presence of either cardiolipin "empty" liposome or "empty" T$_3$-liposome, as in Table I, or a combination of cardiolipin "empty" liposome and uridine phosphate, as in Table II. The presence of the anti-liposomal activity in these serum samples is evident from the data presented.

EXAMPLE III

This Example illustrates the effect of adding cardiolipin "empty" liposomes to the T$_4$ liposome immunoassay.

REAGENTS

Galactosidase-containing T$_4$-liposome, prepared as described in Example I, was used in this experiment. Anti-T$_4$ antiserum and complement were from the same source as described in Example I. Anti-T$_4$ reagent was prepared by diluting the T$_4$ antibody 1:60 with barbital buffer. Complement reagent was prepared by mixing the lyophilized material (one vial) in 3 ml distilled water.

T$_4$ human serum standards (1.5, 3, 6, 12, 24 ug/dl), barbital buffer, "substrate" and "ANS" solution were prepared as described in Example I.

Cardiolipin "empty" liposomes used in this experiment were prepared as described in Example II.

Reagent A was prepared by combining 235 ul of "substrate" and "ANS" stock solution with 40 ul (1:60) antibody and 30 ul (1:30) cardiolipin "empty" liposome and 45 ul barbital buffer. The preparation was scaled up to provide sufficient reagent for multiple testing.

Reagent B, which is a mixture of T$_4$-liposome and complement, was prepared as described in Example I. Here again, the preparation was scaled up to provide sufficient reagent for multiple testing.

ASSAY PROCEDURE AND RESULTS

The assay procedure was as described in Example I.

Twenty clinical samples in the presence of cardiolipin "empty" liposome were evaluated. A correlation with RIA techniques yielded a coefficient of 0.8989 which is significantly improved as compared with that of Example I.

EXAMPLE IV

This Example demonstrates the further improvement of the T$_4$ liposome immunoassay by the addition of cardiolipin "empty" liposome, together with phosphoryl choline.

REAGENTS

T$_4$-β-galactosidase liposome, prepared as described in Example I, was used in this experiment. Anti-T$_4$ and complement were from the same source as described in Example I. Anti-$T_4$ reagent was prepared by diluting the $T_4$ antibody (1:60) with barbital buffer. Complement reagent was prepared by mixing the lyophilized material (one vial) in 3 ml of distilled water.

$T_4$ human serum standards, barbital buffer, "substrate" and "ANS" solution were prepared as described in Example I.

Cardiolipin "empty" liposome was prepared as described in Example II.

Phosphoryl choline solution was prepared by dissolving 13 mg of phosphoryl choline calcium salt (Sigma, supra) in 1 ml of barbital buffer as stock solution. In each immunoassay, 20 uls of the stock phosphoryl choline solution was used.

Reagent A was prepared by combining 235 ul "ONPG" and "ANS" stock solution with 50 ul (1:60) antibody, 30 ul (1:30) cardiolipin "empty" liposome, 20 ul phosphoryl choline stock solution and 15 ul barbital buffer.

Reagent B, which is a mixture of $\beta$-galactosidase-containing $T_4$-liposome, complement, was prepared as described in Example I.

ASSAY PROCEDURE AND RESULTS

The assay procedure was as described in Example I.

Twenty clinical samples with $T_4$ liposome immunoassay (LIA) in the presence of phosphoryl choline and cardiolipin "empty" liposome. The results demonstrated that a further improvement of $T_4$ liposome immunoassay was achieved in the presence of phosphoryl choline and cardiolipin "empty" liposome in the assay. A correlation coefficient of 0.9654 was obtained with RIA technique, indicating suitability of the assay procedure for clinical applications.

What is claimed is:

1. A liposome immunoassay method for determining analyte in a sample with reduced interference from endogenous species comprising the steps of:
    (a) mixing with said sample to form a reaction mixture:
        (i) a first liposome containing an encapsulated marker or component of a marker system and a first ligand or ligand analogue of said analyte incorporated into the membrane of said liposome to provide a first binding domain;
        (ii) a binding partner reactive with said analyte and said first binding domain of said first liposome;
        (iii) at least one substance which modifies the permeability of said first liposome in response to binding of said ligand or ligand analogue and said binding partner; and
        (iv) a second liposome comprising a protein or second ligand analogue of said analyte incorporated into the membrane of said second liposome to provide at least one second binding domain non-cross-reactive with said first binding domain for said binding partner;
    (b) incubating said reaction mixture, wherein binding of said endogenous species to said at least one second binding domain reduces the amount of interfering species which bind to said first liposome;
    (c) measuring said marker from first liposomes displaying modified permeability in response to said at least one substance; and
    (d) relating said measurement to the determination of said analyte.

2. The method of claim 1, comprising the further step of incorporating a cardiolipin within the membrane of said second liposome.

3. The method of claim 1, further including the step of introducing at least one soluble ester of a phosphoric acid into said reaction mixture to provide phosphoryl ester groupings in solution.

4. The method of claim 3, wherein said one soluble ester is phosphoryl choline.

5. The method of claim 1, wherein said marker is an enzyme, and including the further step of mixing a substrate for said enzyme into said reaction mixture.

6. The method of claim 5, including the further step of mixing into said reaction mixture a substance which is reactive with the product resulting from the enzymatic conversion of said substrate.

7. The method of claim 6, wherein said reactive substance is an enzyme different from said enzyme encapsulated within said first liposome.

8. The method of claim 5, wherein said enzyme encapsulated within said first liposome is galactosidase and said substrate is a galactoside.

9. The method of claim 3, wherein said one soluble ester is a nucleoside.

10. The method of claim 3, wherein said one soluble ester is a carbohydrate ester of phosphoric acid.

11. A liposome immunoassay reagent composition for determining the presence of an analyte in a liquid sample suspected of containing interfering endogenous species, which reagent composition comprises:
    (a) a first liposome containing an encapsulated marker or component of a marker system and a first ligand or ligand analogue of said analyte incorporated into the membrane of said liposome to provide a first binding domain;
    (b) a binding partner reactive with said analyte and said first binding domain of said first liposome;
    (c) at least one substance which modifies the permeability of said first liposome in response to binding of said ligand or ligand analogue and said binding partner; and
    (d) a second liposome comprising a protein or second ligand analogue of said analyte incorporated into the membrane of said second liposome to provide at least one second binding domain non-cross-reactive with said first binding domain for said binding partner.

12. The composition of claim 11, wherein said second liposome further incorporates a cardiolipin within its membrane.

13. The composition of claim 11, further including (e) at least one soluble ester of a phosphoric acid.

14. The composition of claim 13, wherein said one soluble ester is a phosphoryl choline.

15. The composition of claim 13, wherein said one soluble ester is a nucleoside.

16. The composition of claim 13, wherein said one soluble ester is a carbohydrate ester of phosphoric acid.

17. The composition of claim 11, wherein said marker is an enzyme.

18. The composition of claim 17, further including a substrate for said enzyme and an additional substance reactive with the product resulting from the enzymatic conversion of said substrate, to indicate a change in permeability of said first liposome.

19. The composition of claim 18, wherein said additional substance is another enzyme.

20. The composition of claim 11, wherein said marker is a substrate for an enzyme.

* * * * *